US012765921B2

(12) United States Patent
Wu

(10) Patent No.: US 12,765,921 B2
(45) Date of Patent: Oct. 20, 2026

(54) SPINE STABILIZATION SYSTEM

(71) Applicant: Taipei Medical University, Taipei City (TW)

(72) Inventor: Meng-Huang Wu, Taipei City (TW)

(73) Assignee: Taipei Medical University, Taipei City (TW)

(*) Notice: Subject to any disclaimer, the term of this patent is extended or adjusted under 35 U.S.C. 154(b) by 235 days.

(21) Appl. No.: 18/725,793

(22) PCT Filed: Dec. 27, 2022

(86) PCT No.: PCT/CN2022/142489
§ 371 (c)(1),
(2) Date: Jun. 30, 2024

(87) PCT Pub. No.: WO2023/125567
PCT Pub. Date: Jul. 6, 2023

(65) Prior Publication Data

US 2025/0099136 A1 Mar. 27, 2025

Related U.S. Application Data

(60) Provisional application No. 63/392,343, filed on Jul. 26, 2022, provisional application No. 63/296,118, filed on Jan. 3, 2022.

(51) Int. Cl.
*A61B 17/70* (2006.01)

(52) U.S. Cl.
CPC ...... *A61B 17/7007* (2013.01); *A61B 17/7026* (2013.01)

(58) Field of Classification Search
CPC ............ A61B 17/7007; A61B 17/7026; A61B 17/7053; A61B 17/0487; A61B 17/8861;
(Continued)

(56) References Cited

U.S. PATENT DOCUMENTS

| | | | |
|---|---|---|---|
| 2005/0124991 | A1 | 6/2005 | Jahng |
| 2005/0267470 | A1 | 12/2005 | McBride |

(Continued)

FOREIGN PATENT DOCUMENTS

| | | | |
|---|---|---|---|
| CM | 214761250 | U | 11/2021 |
| CN | 113040845 | A | 6/2021 |

OTHER PUBLICATIONS

International Search Report mailed on Feb. 20, 2023, International Application No. PCT/CN2022/142489.

*Primary Examiner* — Nicholas J Plionis
(74) *Attorney, Agent, or Firm* — Haverstock & Owens, A Law Corporation

(57) ABSTRACT

The present invention provides a spine stabilization system comprising: a wire; a first fixation member connected to the wire; and an auxiliary fixation device. The auxiliary fixation device comprises: a main body portion; a needle portion connected to the main body portion, wherein a portion of the wire is disposed within the needle portion, and the wire and the first fixation member are able to move relative to the needle portion; a push rod portion partially arranged in the needle portion and is able to move relative to the needle portion; and a control portion connected to the push rod portion. The control portion causes the push rod portion to move relative to the needle portion, so that the wire and the first fixation member move relative to the needle portion by means of the push rod portion.

21 Claims, 15 Drawing Sheets

(58) Field of Classification Search
CPC ........... A61B 2017/00367; A61B 2017/00407; A61B 2017/0409; A61B 2017/0414; A61B 2017/0417; A61B 2017/0464; A61B 2017/0401; A61B 2017/0496; A61F 5/01; A61F 2/4611
See application file for complete search history.

(56) References Cited

U.S. PATENT DOCUMENTS

| | | | | |
|---|---|---|---|---|
| 2009/0112266 | A1 | 4/2009 | Weng et al. | |
| 2010/0094425 | A1* | 4/2010 | Bentley | A61F 2/442<br>606/86 A |
| 2011/0040331 | A1 | 2/2011 | Fernandez | |
| 2012/0053636 | A1 | 3/2012 | Schmocker | |
| 2013/0325071 | A1* | 12/2013 | Niemiec | A61B 17/8866<br>606/279 |
| 2018/0029824 | A1* | 2/2018 | Gephart | A61B 17/8869 |

* cited by examiner

SPINE STABILIZATION SYSTEM

FIELD OF THE INVENTION

The present invention relates generally to a spine stabilization system, and more particularly to a spine stabilization system for fixating an auxiliary wire to a spinal ligament so as to enhance spinal stability.

DESCRIPTION OF THE PRIOR ART

Conventional spinal fixation systems are typically used to fixate a plurality of pedicle screws to the vertebrae, and then the pedicle screws are secured to one another with a connecting rod, so that the effect of fixating the spine in the right position and angle can be achieved. However, such conventional spinal fixation systems could only fixate the vertebrae provided with pedicle screws, but could not provide any supporting effects for the linkage or relative movement between vertebrae (for example, between a vertebra with a pedicle screw and a vertebra without a pedicle screw), leading to the problem of insufficient stability of the spine. In light of this, there is a need to develop a spine stabilization system for fixating an auxiliary wire to spinal ligaments to enhance spinal stability.

SUMMARY OF THE INVENTION

To address the above-described problems, an object of the present invention is to provide a spine stabilization system that can fixate an auxiliary wire to a spinal ligament so as to enhance spinal stability.

Based on the above object, the present invention provides a spine stabilization system comprising: a wire having a first wire end and a second wire end; a first fixation member connected to the first wire end; a wire controller, the second wire end being connected to the wire controller, and a portion of the wire being movably disposed on the wire controller; and a first auxiliary fixation device comprising a needle portion and a first receiving portion, wherein when the spine stabilization system is in a first state of use, the wire together with the wire controller are detachably connected to the first auxiliary fixation device; and wherein when the spine stabilization system is in the first state of use, the wire is partially received in the needle portion, and the wire controller is connected to the first receiving portion of the first auxiliary fixation device.

In a preferred embodiment, the wire is elastic.

In a preferred embodiment, the needle portion is provided with a slot extending thereon, and the wire extends from the slot to the outside of the needle portion and is connected to the wire controller.

In a preferred embodiment, the wire controller comprises a gear portion contacting the first receiving portion, and the wire controller is prevented from moving relative to the first receiving portion in a particular direction by means of the gear portion.

In a preferred embodiment, the wire controller comprises a rod portion and the first receiving portion of the first auxiliary fixation device comprises a first open slot. Moreover, when the spine stabilization system is in the first state of use, the wire controller is detachably connected to the first open slot of the first auxiliary fixation device by means of the rod portion.

In a preferred embodiment, the first auxiliary fixation device comprises a pushing mechanism, and the first auxiliary fixation device pushes the first fixation member outward from within the needle portion by means of the pushing mechanism, so that the first fixation member is fixated to a target spinal ligament.

In a preferred embodiment, the pushing mechanism is that the first auxiliary fixation device consists of a push rod and a push rod passage, and the push rod passage communicates with the needle portion. Moreover, the push rod enters the needle portion through the push rod passage and pushes the first fixation member outward from within the needle portion.

In a preferred embodiment, the spine stabilization system further comprises a plurality of second fixation members, each second fixation member being connected to the wire individually, wherein when the spine stabilization system is in the first state of use, at least one among the first fixation member and the plurality of second fixation members is received in the needle portion.

In a preferred embodiment, the first fixation member comprises a first puncture portion and a first connection portion, and the first fixation member is connected to the wire through the first connection portion. Moreover, each of the plurality of second fixation members comprises a second puncture portion and a second connection portion, and each second fixation member is connected to the wire through a corresponding second connection portion.

In a preferred embodiment, the first auxiliary fixation device comprises a pushing mechanism, and the first auxiliary fixation device pushes one among the first fixation member and the plurality of second fixation members outward from within the needle portion by means of the pushing mechanism, so that the first fixation member and/or the second fixation member is fixated to a target spinal ligament.

In a preferred embodiment, the spine stabilization system further comprises a second auxiliary fixation device comprising a second receiving portion. Moreover, when the spine stabilization system is in a second state of use, the first fixation member is fixated to a target spinal ligament, and the wire together with the wire controller are detachably connected to the second auxiliary fixation device; and when the spine stabilization system is in the second state of use, the wire controller is connected to the second receiving portion of the second auxiliary fixation device.

In a preferred embodiment, the second auxiliary fixation device comprises a wire securing member and a securing mechanism, and the second auxiliary fixation device secures the wire between the wire securing member and a target connecting rod by means of the securing mechanism.

In a preferred embodiment, the wire controller comprises a rod portion and the second auxiliary fixation device comprises a second open slot. Moreover, when the spine stabilization system is in the second state of use, the wire controller is detachably connected to the second open slot of the second auxiliary fixation device by means of the rod portion.

Based on another object, the present invention provides a spine stabilization system comprising: a wire; a first fixation member connected to the wire; and an auxiliary fixation device, the auxiliary fixation device comprising: a main body portion; a needle portion connected to the main body portion, wherein a portion of the wire is disposed within the needle portion, and the wire and the first fixation member are able to move relative to the needle portion; a push rod portion partially arranged in the needle portion and is able to move relative to the needle portion; and a control portion connected to the push rod portion, wherein the control portion causes the push rod portion to move relative to the needle portion, so that the wire and the first fixation member move relative to the needle portion by means of the push rod portion.

In a preferred embodiment, the control portion has a first thread, the push rod portion has a second thread, and the control portion is threadedly connected to the second thread of the push rod portion through the first thread. Moreover, threaded engagement and relative movement between the control portion and the push rod portion causes the push rod portion to move relative to the needle portion.

In a preferred embodiment, the control portion is connected to the main body portion and is able to move relative to the main body portion.

In a preferred embodiment, the main body portion comprises a groove portion having a groove extension direction. Moreover, the push rod portion comprises a groove connection portion partially disposed in the groove portion, and the push rod portion moves relative to the main body portion along the groove extension direction by means of the groove connection portion.

In a preferred embodiment, the auxiliary fixation device comprises a wire controller connected to the main body portion, the wire controller being able to move relative to the main body portion. Moreover, the first fixation member is connected to a first wire end of the wire. Moreover, a second wire end of the wire is connected to the wire controller, and a portion of the wire is movably disposed on the wire controller.

In a preferred embodiment, the needle portion is provided with a slot extending thereon, and the wire extends from the slot to the outside of the needle portion and is connected to the wire controller.

In a preferred embodiment, the wire controller comprises a first securing portion, and the auxiliary fixation device comprises a second securing portion provided on the main body portion, the second securing portion being able to move relative to the main body portion. Moreover, when the second securing portion is in a first state, the second securing portion contacts the first securing portion, so that the wire controller is unable to move relative to the main body portion in a first direction. Moreover, when the second securing portion is in a second state, the second securing portion and the first securing portion are apart from each other.

In a preferred embodiment, the first securing portion is a gear portion provided on the wire controller.

In a preferred embodiment, the wire is elastic.

In a preferred embodiment, the spine stabilization system further comprises a plurality of second fixation members, each second fixation member being connected to the wire individually, wherein at least one among the first fixation member and the plurality of second fixation members is received in the needle portion.

In a preferred embodiment, the first fixation member comprises a puncture portion and a connection portion, and the first fixation member is connected to the wire through the connection portion.

The foregoing aspects and other aspects of the present invention will become more apparent by referring to the description of the non-limiting embodiments given below and the accompanying drawings.

DETAILED DESCRIPTION OF THE PREFERRED EMBODIMENTS

Figure 1:
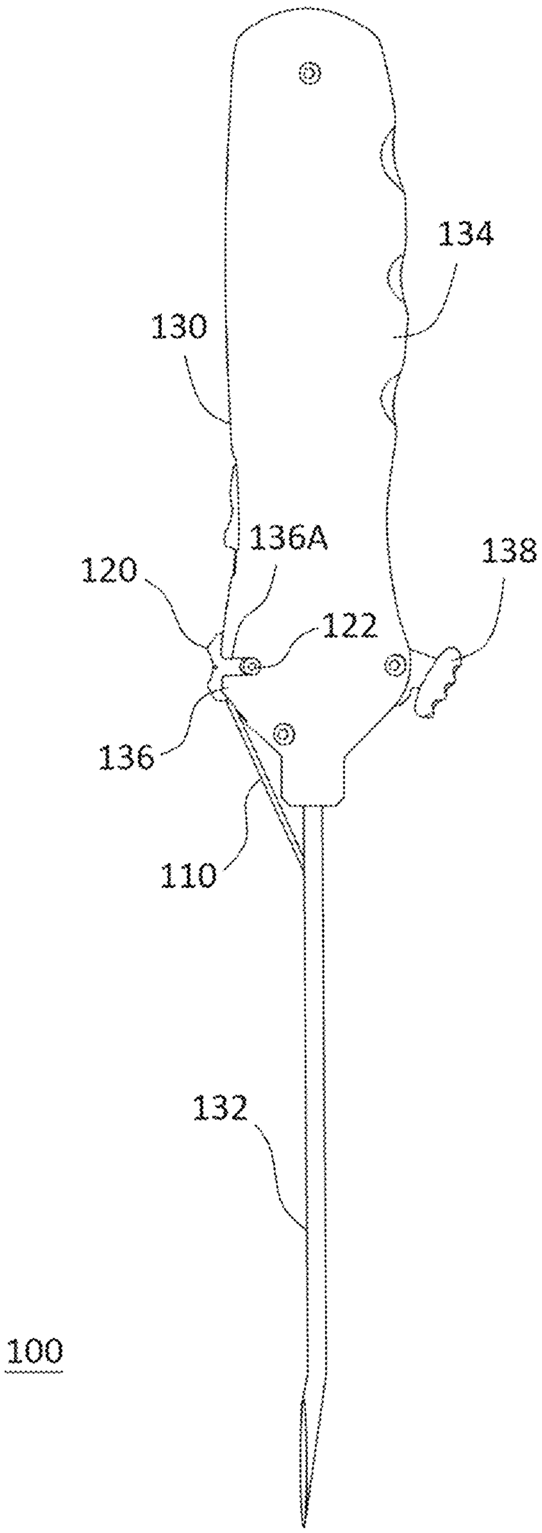
FIG. 1 is a schematic diagram of a spine stabilization system in a first state of use in accordance with an embodiment of the present invention.

Please refer to FIG. 1, which is a schematic diagram of a spine stabilization system in a first state of use in accordance with an embodiment of the present invention. As the embodiment in FIG. 1 shows, the spine stabilization system 100 comprises a wire 110, a fixation member (not shown), a wire controller 120, and a first auxiliary fixation device 130. The wire controller 120 comprises a rod portion 122. The first auxiliary fixation device 130 comprises a needle portion 132, a first body portion 134, a first receiving portion 136, and a first trigger portion 138; the first receiving portion 136 comprises a first open slot 136A. The needle portion 132 is connected to the first body portion 134, and the first receiving portion 136 and the first trigger portion 138 are provided on the first body portion 134. The wire 110 has a first end and a second end; the first end is connected to a fixation member (for example, the first end of the wire 110 can be connected to a first fixation member), and the second end is connected to the wire controller 120. Meanwhile, a part of the wire 110 is movably disposed on the wire controller 120. It should be understood that the second end of the wire 110 is not required to be secured to the wire controller 120; rather, it can be movably connected to or disposed on the wire controller 120 according to the needs. Preferably, the wire 110 is elastic. When the spine stabilization system 100 is in the first state of use, the wire 110 together with the wire controller 120 are detachably (or removably) connected to the first auxiliary fixation device 130 (i.e., the wire 110 together with the wire controller 120 can be directly detached and removed from the first auxiliary fixation device 130). In one embodiment, when the spine stabilization system 100 is in the first state of use, the first end of the wire 110 and a part of the wire 110 are received within the needle portion 132, and the wire controller 120 is connected to (or mounted on) the first receiving portion 136 of the first auxiliary fixation device 130, wherein the rod portion 122 of the wire controller 120 is detachably (or removably) connected to (or received in) the first open slot 136A of the first auxiliary fixation device 130.

In one embodiment, the needle portion 132 may comprise a slot extending on the needle portion 132. The wire 110 can extend from one end of the slot to the outside of the needle portion 132 to be connected to the wire controller 120. In this way, a part of the wire 110 is disposed outside the first auxiliary fixation device 130. In one embodiment, the fixation member can be disposed within the needle portion 132 of the first auxiliary fixation device 130. Meanwhile, the first auxiliary fixation device 130 comprises a pushing mechanism, and the first auxiliary fixation device 130 can push the fixation member (e.g., a first fixation member or a second fixation member) outward from within the needle portion 132 by means of the pushing mechanism, so that the fixation member can be fixated to the target spinal ligament. In one embodiment, when the first trigger portion 138 of the first auxiliary fixation device 130 is triggered, the first auxiliary fixation member 130 pushes the fixation member outward from within the needle 132 by means of the pushing mechanism. For examples of the pushing mechanism and/or the first trigger portion and/or a related mechanism, please refer to the following patent documents: U.S. Pat. No. 10,363,024B2 (application Ser. No. 14/608,623, entitled “System for meniscal repair using suture implant cinch construct”); U.S. Pat. No. 10,478,175B2 (application Ser. No. 15/208,341, entitled “Method and apparatus for meniscal repair”); U.S. Patent Application Publication No. 20190343509A1 (application Ser. No. 16/523,382, entitled “System for meniscal repair using suture implant cinch construct”); U.S. Patent Application Publication No. 20200069307A1 (application Ser. No. 16/675,927, entitled “Method and apparatus for meniscal repair”); and China Patent Application Publication No. 112839594A (application Ser. No. 201980066558.0, entitled “System for repairing soft tissue tears), all of which are incorporated herein by reference.

Figure 2A:
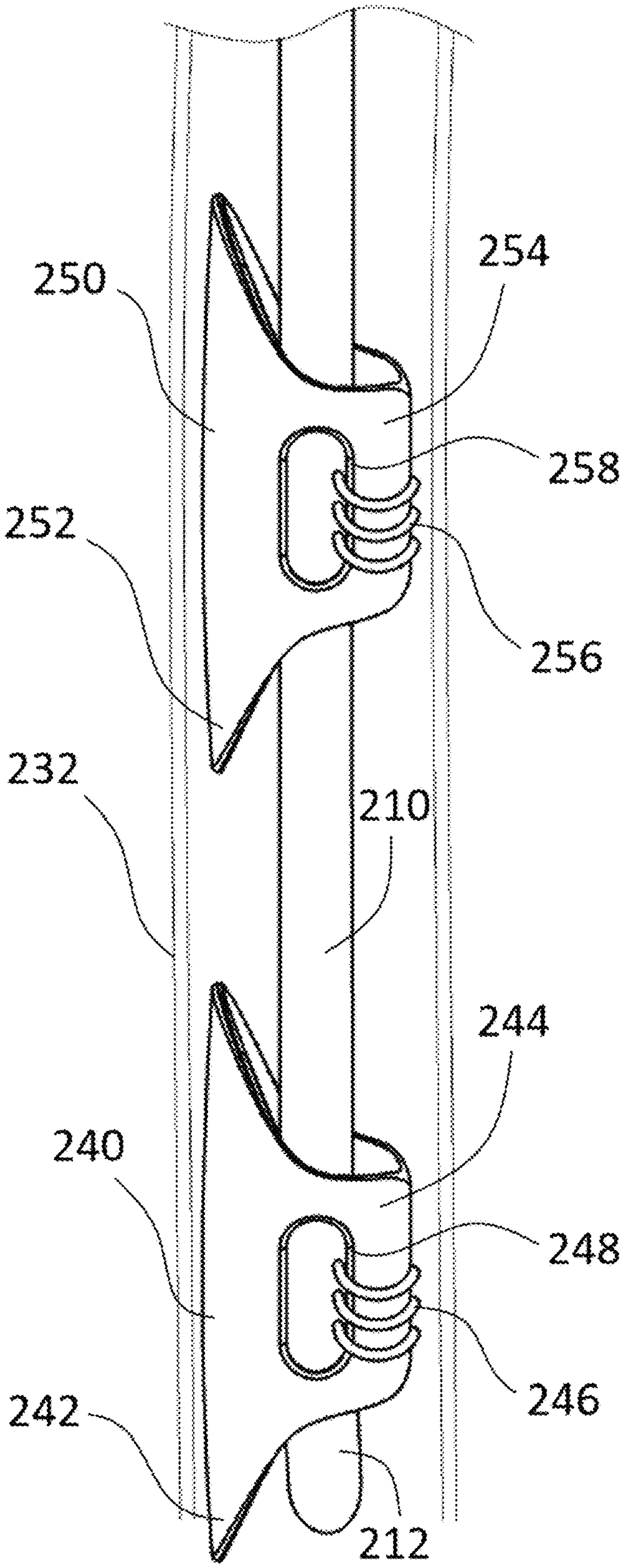
FIG. 2A is a schematic diagram showing a wire and fixation members of the spine stabilization system in accordance with an embodiment of the present invention.

Please refer to FIG. 2A, which is a schematic diagram showing a wire and fixation members of the spine stabilization system in accordance with an embodiment of the present invention. As the embodiment in FIG. 2A shows, a first fixation member 240 comprises a first puncture portion 242 and a first connection portion 244; a first connection hole 248 is provided on the first connection portion 244. A second fixation member 250 comprises a second puncture portion 252 and a second connection portion 254; a second connection hole 258 is provided on the second connection portion 254. A wire 210 is connected to the first connection portion 244 of the first fixation member 240, and the wire 210 is also connected to the second connection portion 254 of the second fixation member 250. Specifically, the first fixation member 240 is connected to a first end 212 of the wire 210, and the second fixation member 250 is connected to another position on the wire 210. In one embodiment, the first fixation member 240 can puncture and penetrate the target spinal ligament by the first puncture portion 242, thereby fixating the first fixation member 240 to the target spinal ligament. The second fixation member 250 can puncture and penetrate the target spinal ligament by the second puncture portion 252, thereby fixating the second fixation member 250 to the target spinal ligament. Preferably, in the course of fixating a fixation member (e.g., the first fixation member or the second fixation member) to a target spinal ligament, the first auxiliary fixation device can first push the puncture portion of the fixation member (e.g., the first fixation member or the second fixation member) to the front end of a needle portion 232 by means of the pushing mechanism, so that the puncture portion is exposed to the outside of the needle portion 232. After the puncture portion punctures the target spinal ligament, the fixation member is then pushed out entirely by the pushing mechanism, so that the fixation member penetrates the target spinal ligament and is fixated thereon.

In one embodiment, the first fixation member 240 may comprise a first auxiliary connection portion 246. The first connection portion 246 can pass through the first connection hole 248 and the wire 210, thereby enabling the first fixation member 240 to be connected to the wire 210. The second fixation member 250 may comprise a second auxiliary connection portion 256. The second auxiliary connection portion 256 can pass through the second connection hole 258 and the wire 210, thereby enabling the second fixation member 250 to be connected to the wire 210. It should be understood that the method for connecting the first fixation member 240 or the second fixation member 250 to the wire 210 is not limited to the one shown in FIG. 2; the first fixation member and the second fixation member can be connected to the wire in other ways. For example, the wire can directly pass through the connection portion (e.g., the first connection portion or the second connection portion) of the fixation member (e.g., the first fixation member or the second fixation member) and be connected to the fixation member by winding and/or knotting. Methods for connecting the wire and the fixation member can be found in, for example, the U.S. and Chinese patent documents mentioned above, but are not limited thereto. It should be understood that the number of fixation members connected to the wire 210 is not limited to merely two; rather, one or more fixation members can be connected to the wire 210 according to the needs. For example, there may be only one first fixation member 240 connected to the wire 210 at the first end 212, while the rest of the wire is not connected to any fixation member. Alternatively, the wire may be connected to one first fixation member at the first end, while multiple second fixation members are connected separately to the wire at various other positions. Preferably, when the spine stabilization system is in the first state of use, at least one among the first fixation member and the plurality of second fixation members is received within the needle portion. For example, when the spine stabilization system is in the first state of use, the fixation member for the target spinal ligament to be punctured is received within the needle portion. Preferably, the first fixation member and each of the second fixation members connected to the wire may have the same structure.

Figure 2B:
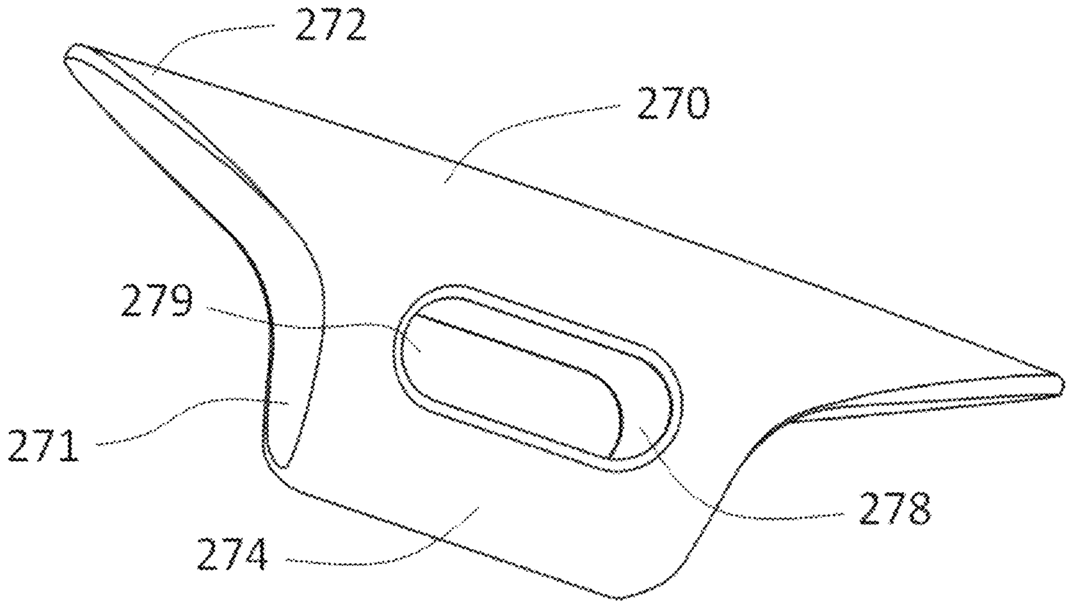
FIG. 2B is a schematic diagram of a fixation member of the spine stabilization system in accordance with an embodiment of the present invention.
Figure 3:
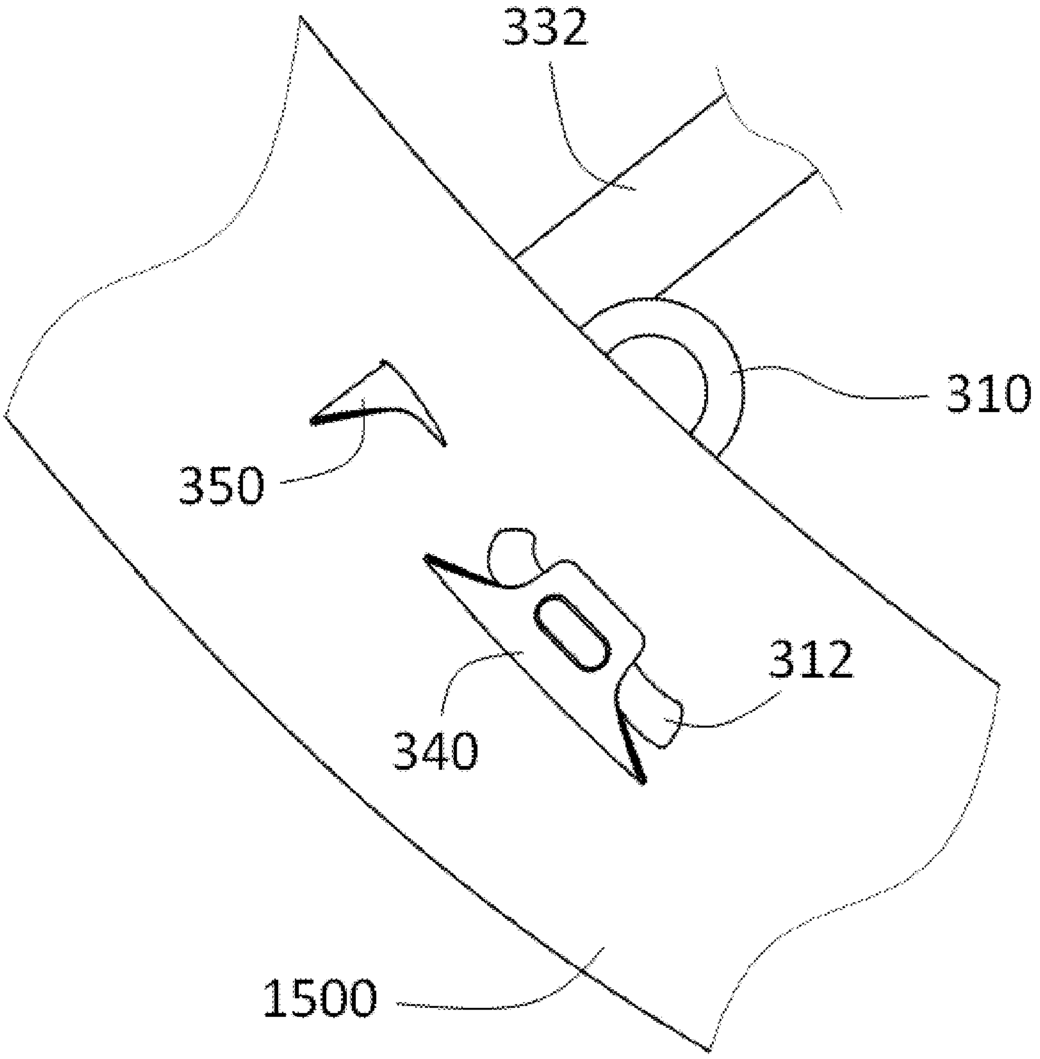
FIG. 3 is a schematic diagram showing a fixation member being fixated to a spinal ligament in accordance with an embodiment of the present invention.

Please refer to FIG. 2B, which is a schematic diagram of a fixation member of the spine stabilization system in accordance with an embodiment of the present invention. As the embodiment in FIG. 2B shows, a fixation member 270 comprises a puncture portion 272 and a connection portion 274, and a wire connection hole 271 and connection holes 278, 279 are provided on the connection portion 274. The wire can pass through the wire connection hole 271 and/or connection holes 278, 279. Please refer to FIG. 3, which is a schematic diagram showing a fixation member being fixated to a spinal ligament in accordance with an embodiment of the present invention. As the embodiment in FIG. 3 shows, a wire 310 is connected to both a first fixation member 340 and a second fixation member 350, wherein the first fixation member 340 is connected to a first end 312 of the wire 310. The first fixation member 340 punctures and penetrates a target spinal ligament 1500 and is fixated thereon. A second puncture portion of the second fixation member 350 is exposed to the outside of the needle portion 332, and it punctures and penetrates the target spinal ligament 1500.

Figure 4:
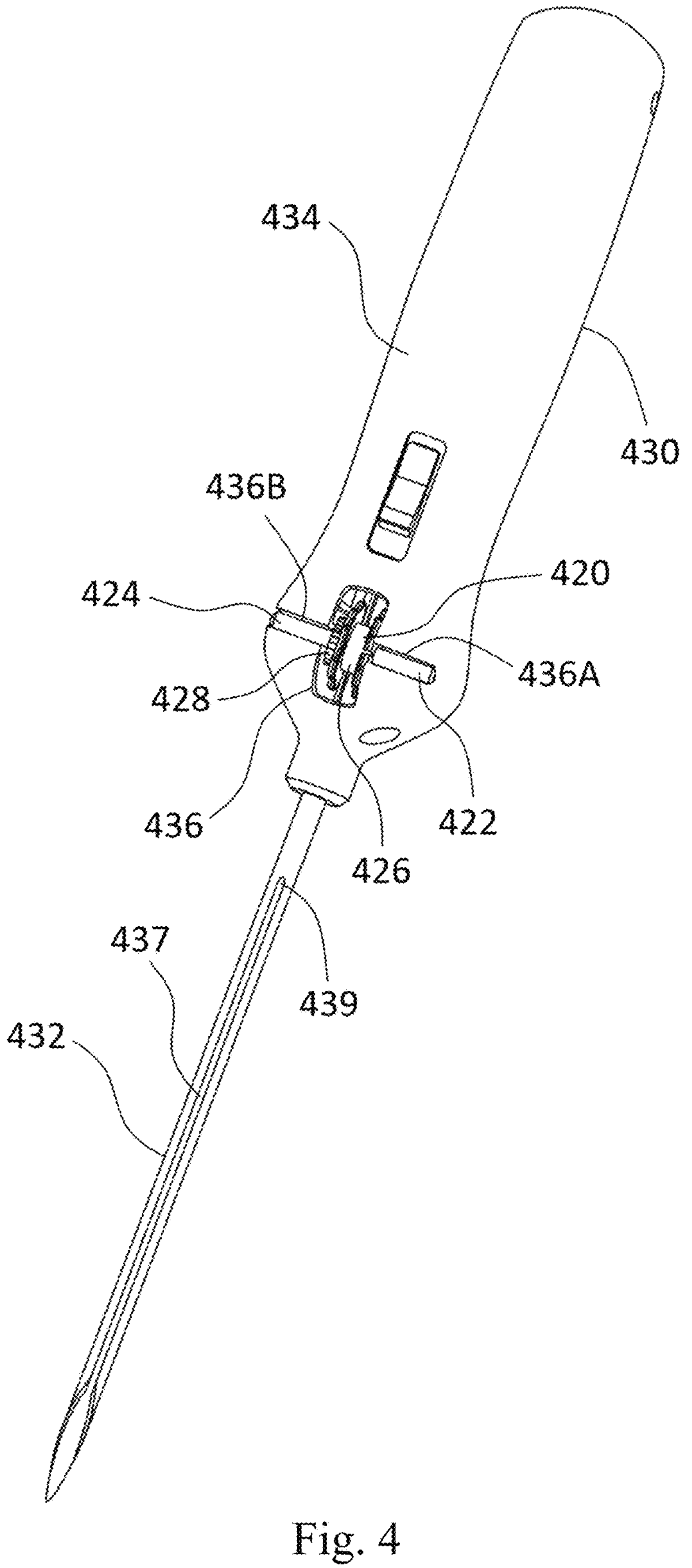
FIG. 4 is a schematic diagram of a wire controller and a first auxiliary fixation device of the spine stabilization system in accordance with an embodiment of the present invention.

Please refer to FIG. 4, which is a schematic diagram of a wire controller and a first auxiliary fixation device of the spine stabilization system in accordance with an embodiment of the present invention. As the embodiment in FIG. 4 shows, a wire controller 420 comprises rod portions 422 and 424, a wire receiving portion 426 and a gear portion 428; the wire receiving portion 426 is connected to the rod portions 422 and 424, and is also connected to the gear portion 428. A first auxiliary fixation device 430 comprises a needle portion 432, a first body portion 434, and a first receiving portion 436; the needle portion 432 is connected to the first body portion 434, and the first receiving portion 436 is provided on the first body portion 434. The needle portion 432 has a slot 437 extending thereon. When the spine stabilization system is in the first state of use, the wire can be partially received within the needle portion 432. The wire can also extend from a slot end 439 of the slot 437 to the outside of the needle portion 432, and is then connected to and received in (such as being wound around) the wire receiving portion 426 of the wire controller 420. The first receiving portion 436 comprises first open slots 436A and 436B, and the rod portions 422 and 424 of the wire controller 420 can be received in the first open slots 436A and 436B, respectively, so that the wire controller 420 is connected to and received in the first receiving portion 436 of the first auxiliary fixation device 430.

The gear portion 428 of the wire controller 420 can contact a stop portion on the first receiving portion 436 (such as a protruding block or a spring sheet, but is not limited thereto). Thus, the wire controller 420 can be prevented from moving relative to the first receiving portion 436 in a particular direction by means of the gear portion 428. For example, by means of the gear portion 428, the wire controller 420 can be prevented from rotating relative to the first receiving portion 436 in a particular direction, so that unintended reeling-in of the wire wound around the wire receiving portion 426 during surgery can be avoided (in another embodiment, unintended reeling-out of the wire wound around the wire receiving portion 426 during surgery is to be avoided).

Figure 5:
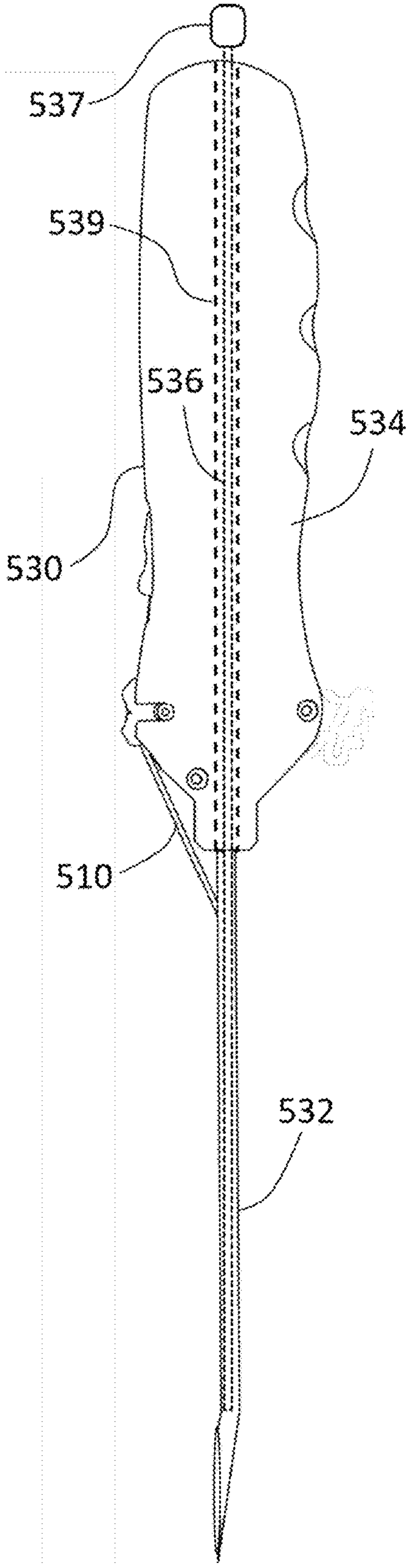
FIG. 5 is a schematic diagram of a first auxiliary fixation device of the spine stabilization system in accordance with an embodiment of the present invention.

Please refer to FIG. 5, which is a schematic diagram of a first auxiliary fixation device of the spine stabilization system in accordance with an embodiment of the present invention. As the embodiment in FIG. 5 shows, a first auxiliary fixation device 530 comprises a needle portion 532, a first body portion 534, and a push rod 536. The needle portion 532 is connected to the first body portion 534, which has a push rod passage 539 therein; the push rod passage 539 communicates with the inside of the needle portion 532. A user may grip the grip portion 537 of the push rod 536 to control the push rod 536, thereby causing the push rod 536 to enter the needle portion 532 through the push rod passage 539 and push the fixation member (not shown) connected to the wire 510 out of the needle portion 532 from the inside.

Figure 6:
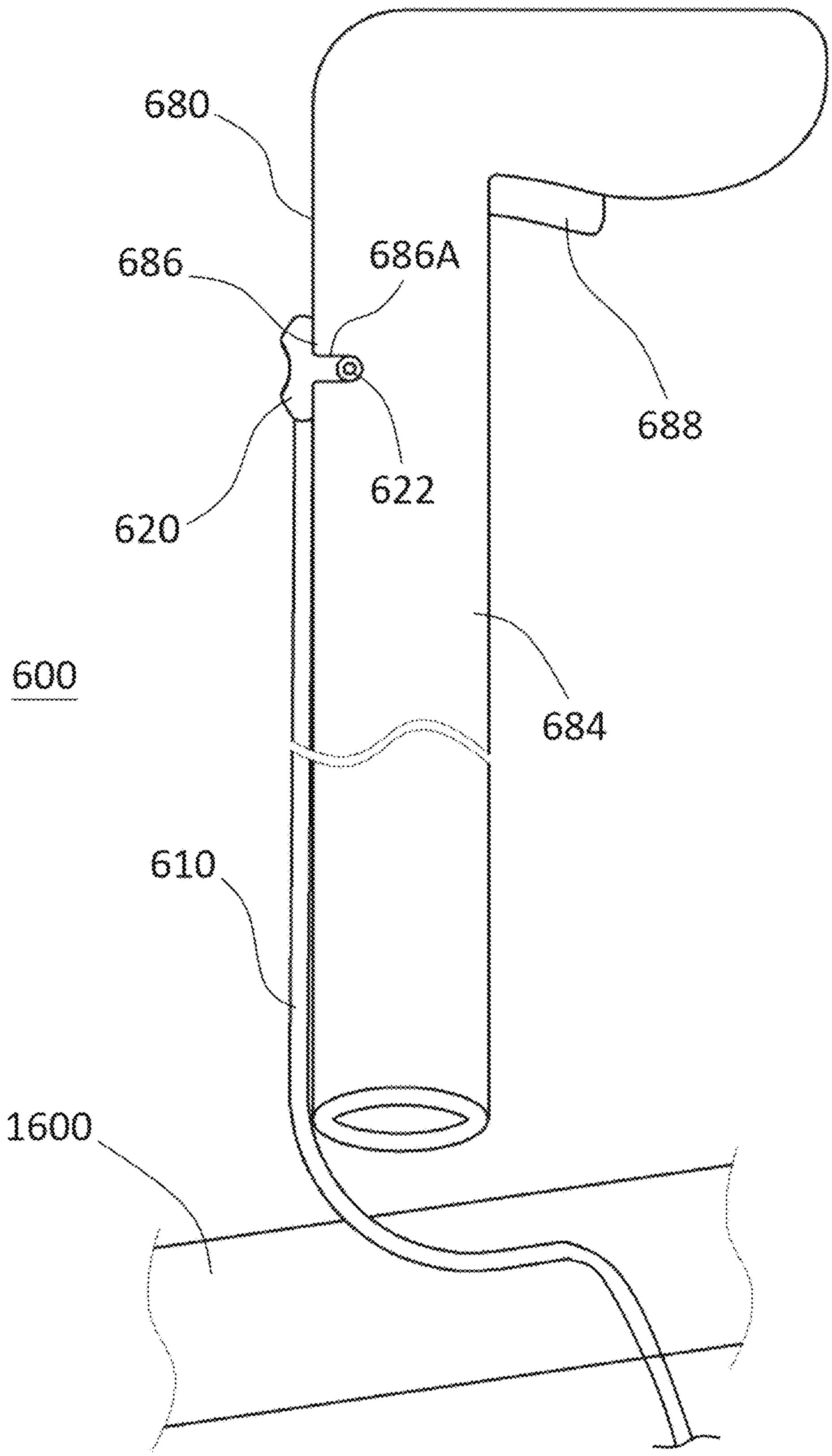
FIG. 6 is a schematic diagram of a spine stabilization system in a second state of use in accordance with an embodiment of the present invention.

Please refer to FIG. 6, which is a schematic diagram of a spine stabilization system in a second state of use in accordance with an embodiment of the present invention. As the embodiment in FIG. 6 shows, the spine stabilization system 600 comprises a wire 610, a wire controller 620, and a second auxiliary fixation device 680. The wire controller 620 comprises a rod portion 622. The second auxiliary fixation device 680 comprises a second body portion 684, a second receiving portion 686, a wire securing member (not shown), and a second trigger portion 688. The second receiving portion 686 comprises a second open slot 686A. The second receiving portion 686 and the second trigger portion 688 are provided on the second body portion 684. A second end of the wire 610 is connected to the wire controller 620. Meanwhile, a part of the wire 610 is movably disposed on the wire controller 620. When the spine stabilization system 600 is in the second state of use, the wire 610 together with the wire controller 620 are detachably (or removably) connected to the second auxiliary fixation device 680 (i.e., the wire 610 together with the wire controller 620 can be directly detached and removed from the second auxiliary fixation device 680). In one embodiment, when the spine stabilization system 600 is in the second state of use, the wire controller 620 is connected to (or mounted on) the second receiving portion 686 of the second auxiliary fixation device 680. Specifically, the rod portion 622 of the wire controller 620 is detachably (or removably) connected to (or received in) the second open slot 686A of the second auxiliary fixation device 680. It should be understood that the method for connecting the wire controller 620 to the second auxiliary fixation device 680 can be similar to or the same as the method for connecting the wire controller 620 to the first auxiliary fixation device.

In one embodiment, the wire securing member is disposed inside the second body portion 684. The user may dispose a part of the wire at the front of the second body portion 684 and then trigger the second trigger portion 688 (the second trigger portion 688 can be regarded as a fixation mechanism of the second auxiliary fixation device 680). When the user triggers the second trigger portion 688, the second auxiliary fixation device 680 pushes (or ejects) the wire securing member outward from the inside of the second body portion 684, and then the wire can be secured between the wire securing member and a target connecting rod. The target connecting rod may include, for example, a connecting rod for connecting two pedicle screws, or surrounding elements of such a connecting rod. Examples of the connecting rod for connecting two pedicle screws and surrounding elements of the connecting rod can be found in the following patent documents: U.S. Pat. No. 6,368,320B1 (application Ser. No. 09/581,104, entitled "Connector for backbone osteosynthesis device"); U.S. Pat. No. 9,949,768B2 (application Ser. No. 15/344,952, entitled "Transconnector"); and U.S. Patent Application Publication No. 20170086889A1 (application Ser. No. 14/864,507, entitled "Spinal implant system and method"), all of which are incorporated herein by reference.

Figure 7:
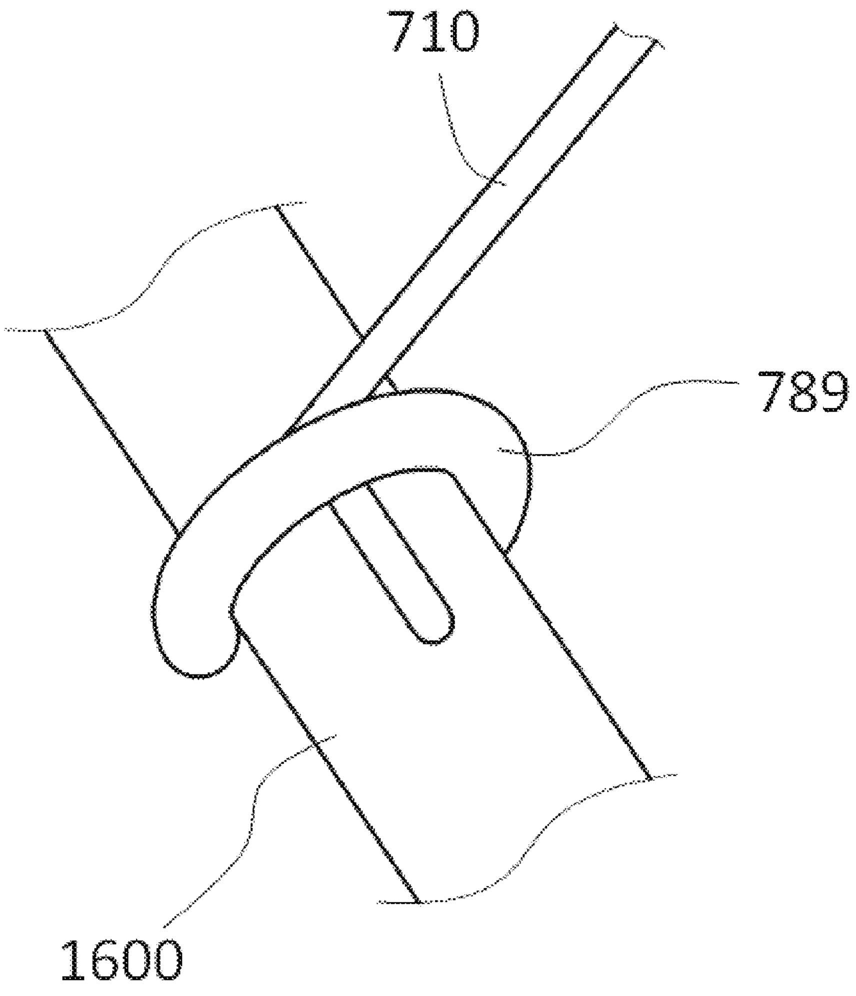
FIG. 7 is a schematic diagram of a wire securing member in accordance with an embodiment of the present invention.

In one embodiment, the second auxiliary fixation device may not comprise a second trigger portion. Rather, it may comprise a second push rod (the second push rod can be regarded as a securing mechanism of the second auxiliary fixation device) to push the wire securing member toward the outside of the second body portion. The structure and pushing mechanism of the second push rod can be similar to or the same as the structure and pushing mechanism of the push rod 536 shown in FIG. 5. Please refer to FIG. 7, which is a schematic diagram of a wire securing member in accordance with an embodiment of the present invention. As the embodiment in FIG. 7 shows, a wire 710 can be secured between a wire securing member 789 and a target connecting rod 1600 by means of the securing mechanism of the second auxiliary fixation device.

Figure 8:
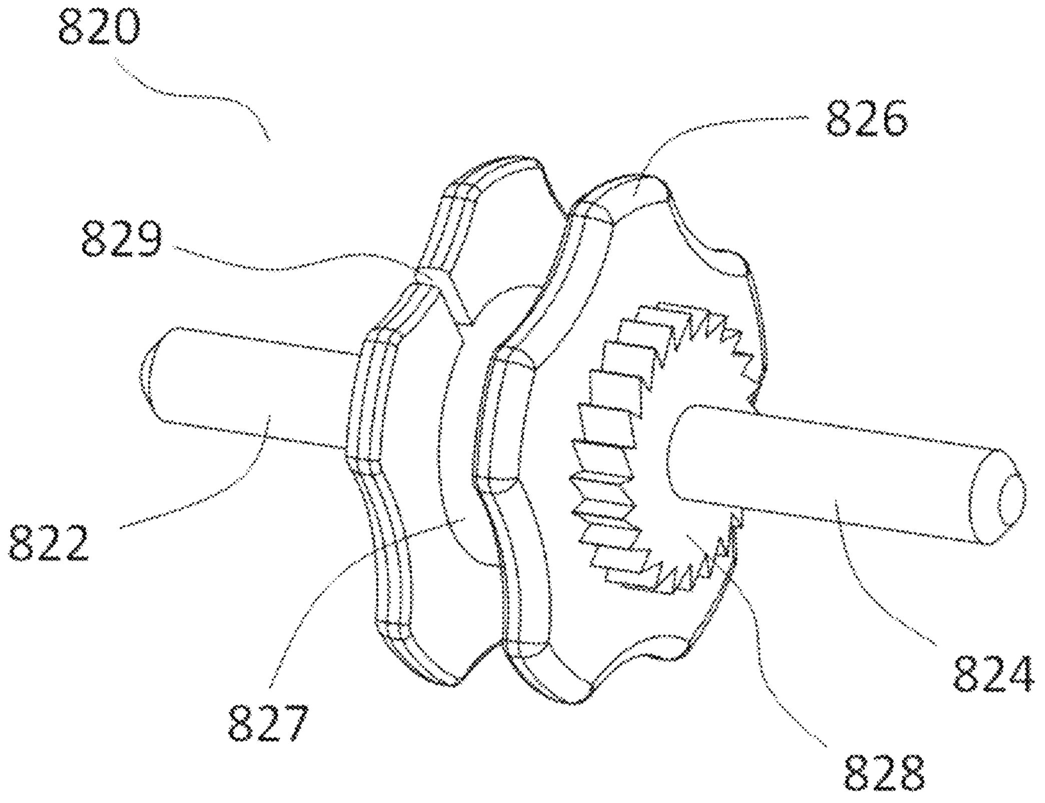
FIG. 8 is a schematic diagram of a wire controller of the spine stabilization system in accordance with an embodiment of the present invention.

Please refer to FIG. 8, which is a schematic diagram showing a wire controller of the spine stabilization system in accordance with an embodiment of the present invention. As the embodiment in FIG. 8 shows, the wire controller 820 comprises rod portions 822 and 824, a wire receiving portion 826, and a gear portion 828. The wire receiving portion 826 comprises an intermediate portion 827 and a wire securing portion 829. The wire receiving portion 826 is connected to the rod portions 822 and 824 (the rod portion 824 can be regarded as passing through the gear portion 828 to connect to the wire receiving portion 826, or regarded as connected to the gear portion 828), and the wire receiving portion 826 is also connected to the gear portion 828. The wire may be clamped to the wire securing portion 829 of the wire receiving portion 826 to prevent the wire from falling off the wire receiving portion 826. Alternatively, the wire may be wound around the intermediate portion 827 of the wire receiving portion 826. When the spine stabilization system is in the first state of use, the rod portions 822 and 824 can be received in the first open slot of the first auxiliary fixation device, and the gear portion 828 can be in contact with a first stop portion on the first receiving portion of the first auxiliary fixation device. When the spine stabilization system is in the second state of use, the rod portions 822 and 824 can be received in the second open slot of the second auxiliary fixation device, and the gear portion 828 can be in contact with a second stop portion on the second receiving portion of the second auxiliary fixation device. Specifically, the function of the second stop portion can be similar to or the same as that of the first stop portion.

Figure 9:
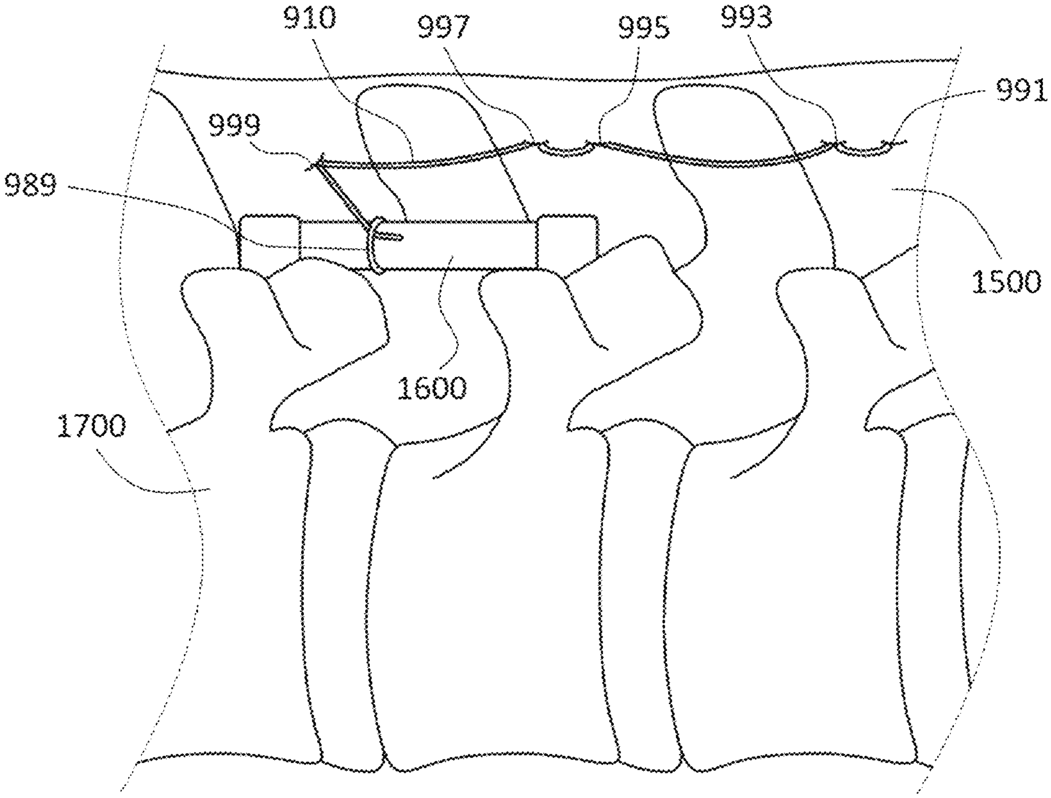
FIG. 9 is a schematic diagram showing a wire, fixation members, and a wire securing member of the spine stabilization system being applied to a target spinal ligament in accordance with an embodiment of the present invention.

Please refer to FIG. 9, which is a schematic diagram showing a wire, fixation members, and a wire securing member of the spine stabilization system being applied to a target spinal ligament in accordance with an embodiment of the present invention. As the embodiment in FIG. 9 shows, when the spine stabilization system is in the first state of use, each of the fixation members on a wire 910 is sequentially fixated to a target spinal ligament 1500 at positions 991, 993, 995, 997 and 999 by means of the first auxiliary fixation device. Then, when the spine stabilization system is in the second state of use, the wire 910 is secured between a wire securing member 989 and a target connecting rod 1600 by means of the second auxiliary fixation device. Afterwards, the excess part of the wire is cut off. In this way, the wire 910 fixated to the target spinal ligament 1500 can help enhance the stability of a target spine 1700. Preferably, the wire 910 is elastic.

Figure 10A:
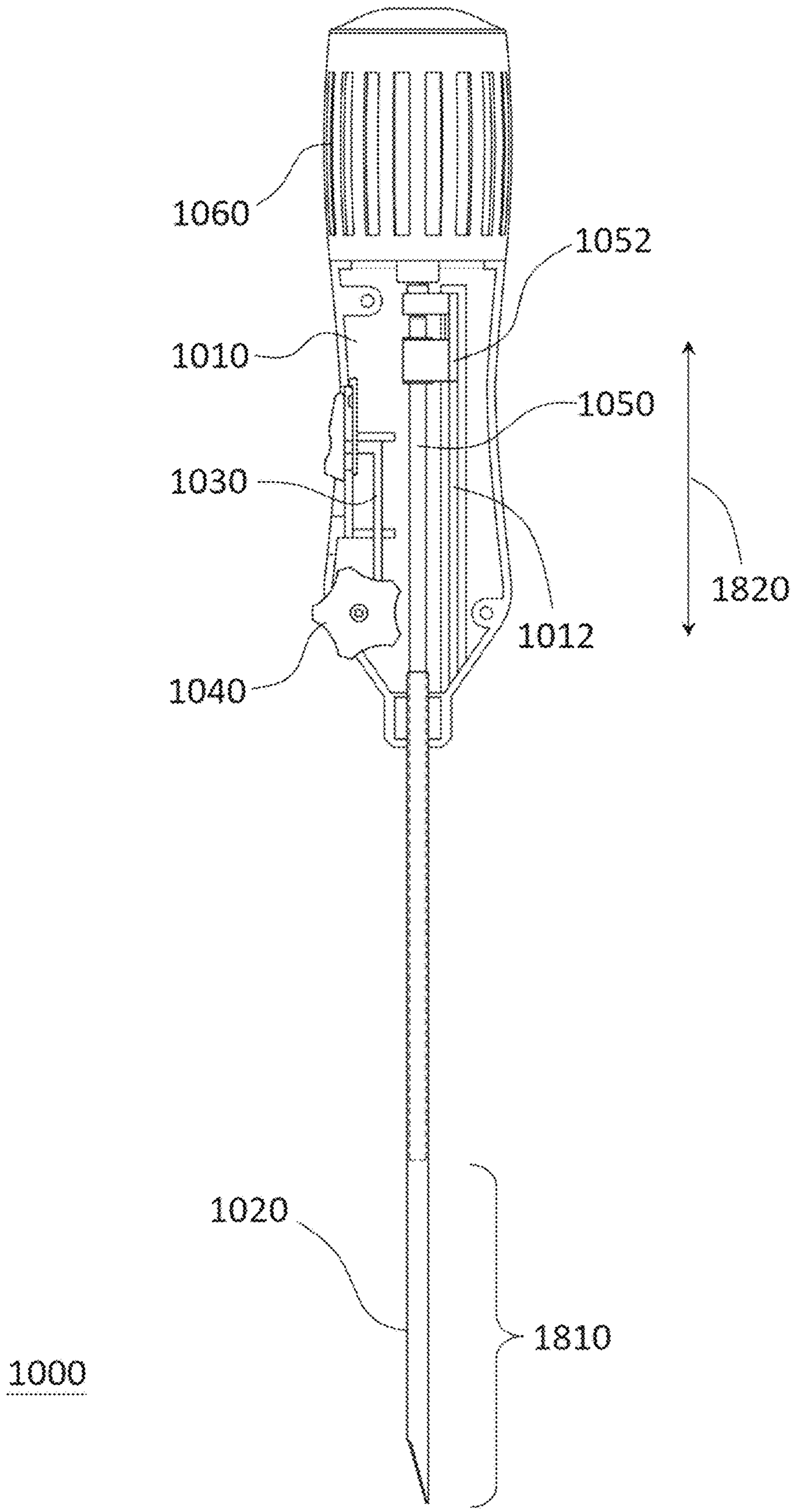
FIG. 10A is a schematic diagram of a spine stabilization system in accordance with an embodiment of the present invention.
Figure 10B:
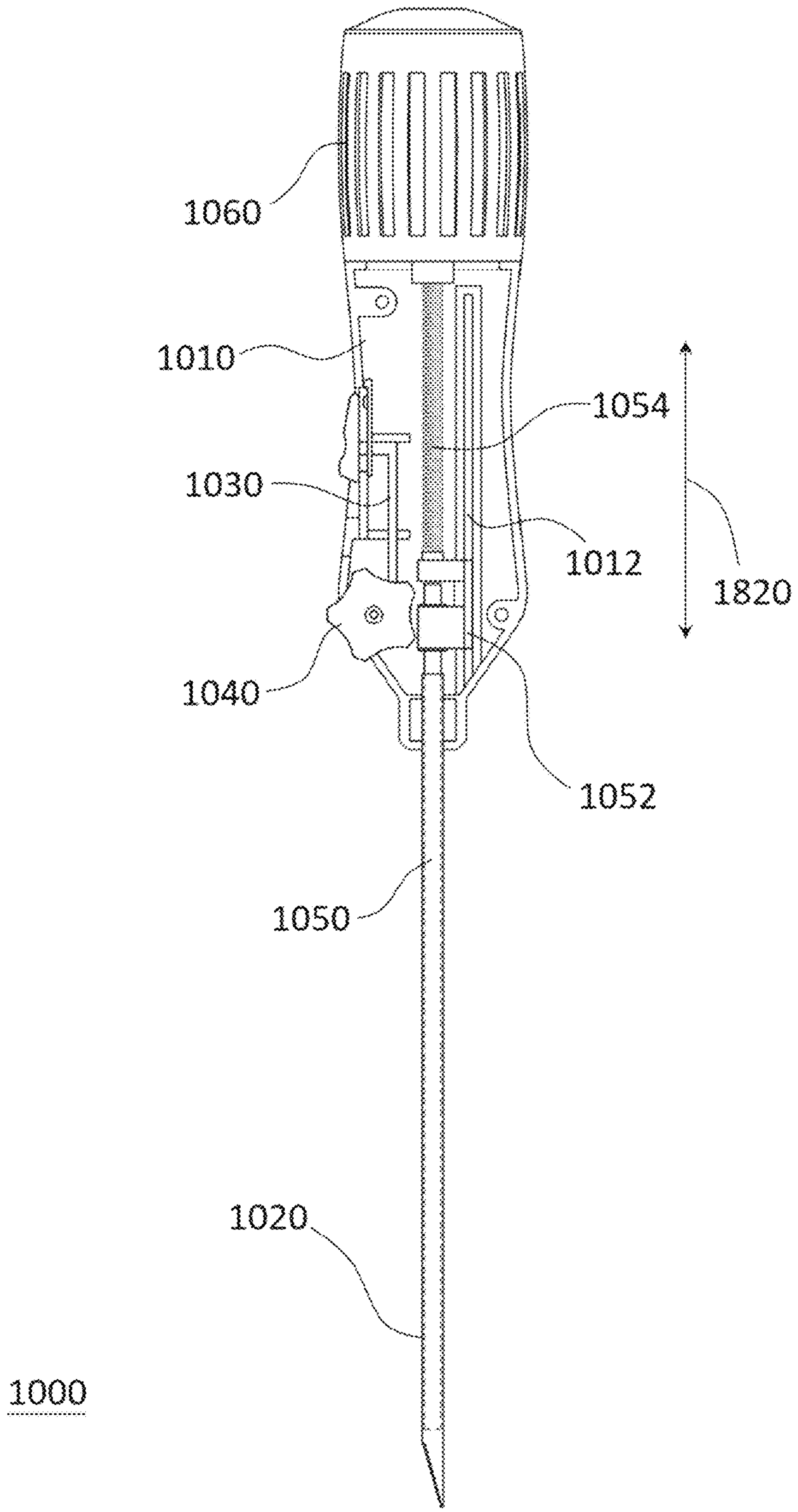
FIG. 10B is a schematic diagram of the spine stabilization system in accordance with an embodiment of the present invention.

Please refer to FIGS. 10A and 10B, which are schematic diagrams of a spine stabilization system in accordance with an embodiment of the present invention. As the embodiment in FIGS. 10A and 10B shows, the spine stabilization system 1000 comprises a wire (now shown), a first fixation member (not shown), and an auxiliary fixation device. The auxiliary fixation device comprises a main body portion 1010, a needle portion 1020, a push rod portion 1050, and a control portion 1060. The first fixation member is connected to the wire, and a part of the wire is received within the needle portion 1020 (before being fixated to a target spinal ligament, the first fixation member together with the part of the wire can also be received within the needle portion 1020, until they are pushed out of the needle portion 1020 by the push rod portion 1050); the wire and the first fixation member can move relative to the needle portion. Preferably, the wire is elastic. Preferably, the fixation member comprises a puncture portion and a connection portion, and the fixation member can be connected to the wire through the connection portion. Methods for connecting the wire and a first fixation member can be seen in FIGS. 2A and 2B as examples, but the connection methods are not limited thereto. Different embodiments of the fixation member can be seen in FIGS. 2A and 2B, which depict non-limiting examples. It should be understood that the number of fixation member used in the spine stabilization system 1000 is not limited to one only; rather, a plurality of fixation members can be used according to the needs. For example, the spine stabilization system 1000 may comprise a first fixation member and a plurality of second fixation members, and each of the plurality of second fixation members is connected to the wire separately. In the course of using the spine stabilization system 1000, at least one among the first fixation member and the plurality of second fixation members is received within the needle portion 1020 (received in the receiving space 1810 at the front part of the push rod portion 1050, for example). In this way, the user can push one among the first fixation member and the plurality of second fixation members outward from within the needle portion 1020 by means of the push rod portion 1050, so that the pushed fixation member can be fixated to the target spinal ligament.

In the embodiment shown in FIGS. 10A and 10B, the needle portion 1020 is connected to the main body portion 1010, the push rod portion 1050 is partially disposed in the needle portion 1020, and the push rod portion 1050 can move relative to the needle portion 1020. The control portion 1060 is connected to the push rod portion 1050, and the control portion 1060 can cause the push rod portion 1050 to move relative to the needle portion 1020, thereby causing the wire and the fixation member (such as the first fixation member) to move relative to the needle portion 1020 by means of the push rod portion 1050. In this way, the user can use the control portion 1060 to cause the push rod portion 1050 to move relative to the needle portion 1020, thereby pushing the fixation member and/or the wire outward from within the needle portion 1020 by means of the push rod portion 1050.

Figure 10C:
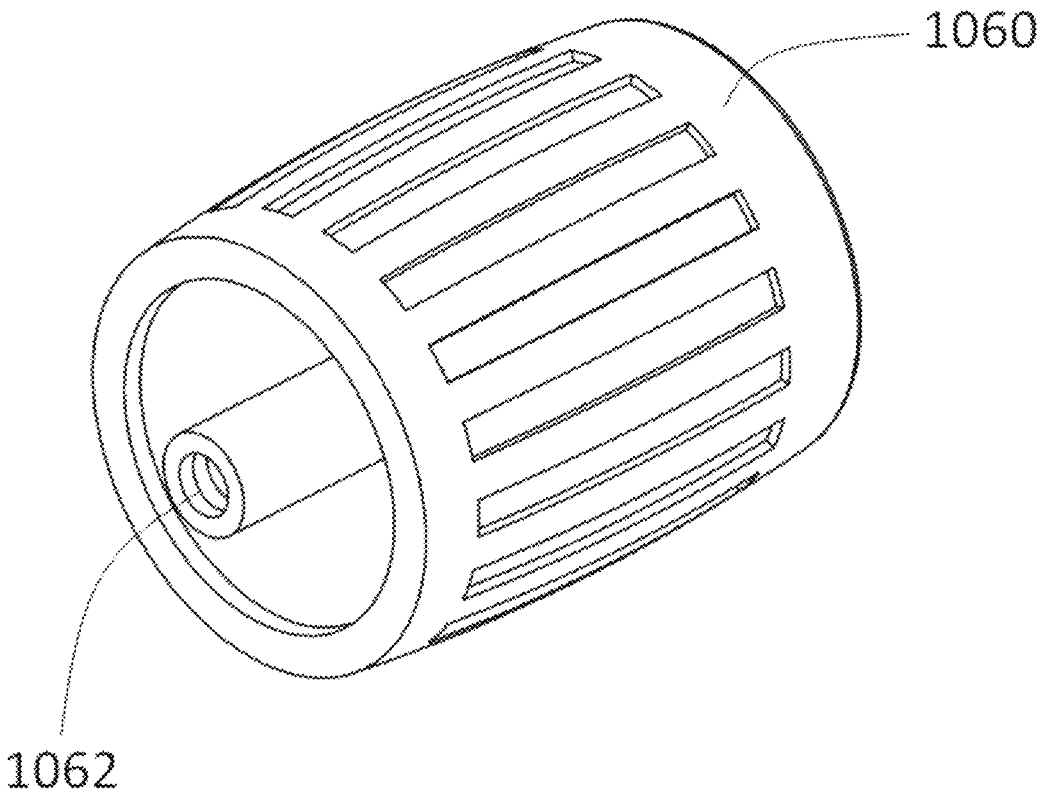
FIG. 10C is a schematic diagram of a control portion of the spine stabilization system in accordance with an embodiment of the present invention.

In one embodiment, the control portion 1060 comprises a first thread (as shown in FIG. 10C, the control portion 1060 comprises a first thread 1062), and the push rod portion 1050 comprises a second thread 1054. The control portion 1060 can be threadedly connected to the second thread 1054 of the push rod portion 1050 through the first thread 1062; the control portion 1060 and the push rod portion 1050 can have threaded engagement and relative movement between them, thereby causing the push rod portion 1050 to move relative to the needle portion 1020. Preferably, the needle portion 1020 is connected to the main body portion 1010, the control portion 1060 is also connected to the main body portion 1010, and the control portion 1060 can move relative to the main body portion 1010. Such arrangement can ensure that during the course of threaded engagement and relative movement between the control portion 1060 and the push rod portion 1050, the push rod portion 1050 will move relative to the needle portion 1020. FIG. 10A illustrates that by means of the threaded engagement and relative movement between the control portion 1060 and the push rod portion 1050, the spine stabilization system 1000 causes the push rod portion 1050 to move toward the control portion 1060. FIG. 10B illustrates that by means of the threaded engagement and relative movement between the control portion 1060 and push rod portion 1050, the spine stabilization system 1000 causes the push rod portion 1050 to move toward the tip of the needle portion 1020.

In one embodiment, the main body portion 1010 comprises a groove portion 1012 that extends in the main body portion 1010 along a groove extension direction 1820 (alternatively, the groove portion 1012 can be regarded as having a groove extension direction 1820). The push rod portion 1050 comprises a groove connection portion 1052 that is partially disposed in the groove portion 1012. In this way, the push rod portion 1050 can move relative to the main body portion 1010 along the groove extension direction 1820 by means of the groove connection portion 1052. The groove connection portion 1052 may, for example, be a protrusion protruding outward from the surface of the push rod portion 1050, but is not limited thereto.

In one embodiment, the auxiliary fixation device comprises a wire controller 1040, which is connected to the main body portion 1010 and can move relative to the main body portion 1010. A fixation member (such as the first fixation member) can be connected to the first wire end of the wire, while the second wire end of the wire can be connected to the wire controller 1040, and a part of the wire is movably disposed (such as being wound around) on the wire controller 1040. Preferably, a part of the wire can be wound on the wire controller 1040. In this way, the wire controller 1040 can be similar to a winder for the wire. It should be understood that the wire controller 1040 may be detachably connected to the main body portion 1010 of the auxiliary fixation device according to the needs, or may be connected to the main body portion 1010 of the auxiliary fixation device in a non-detachable manner according to the needs.

In one embodiment, the needle portion 1020 may comprise a slot extending thereon. The wire can extend from the slot to the outside of the needle portion 1020 to be connected to the wire controller 1040. However, it should be understood that the wire may not extend toward the outside of the needle portion 1020 according to the needs. For example, a part of the wire can be disposed within the needle portion 1020 and the main body portion 1010 and extend therein according to the needs, and then the wire can extend from within the main body portion 1010 to the wire controller 1040 to be disposed thereon (such as being wound around the wire controller 1040). It should be understood that in such practices where the wire does not extend toward the outside of the needle portion 1020, the needle portion may not comprise a slot.

Figure 10D:
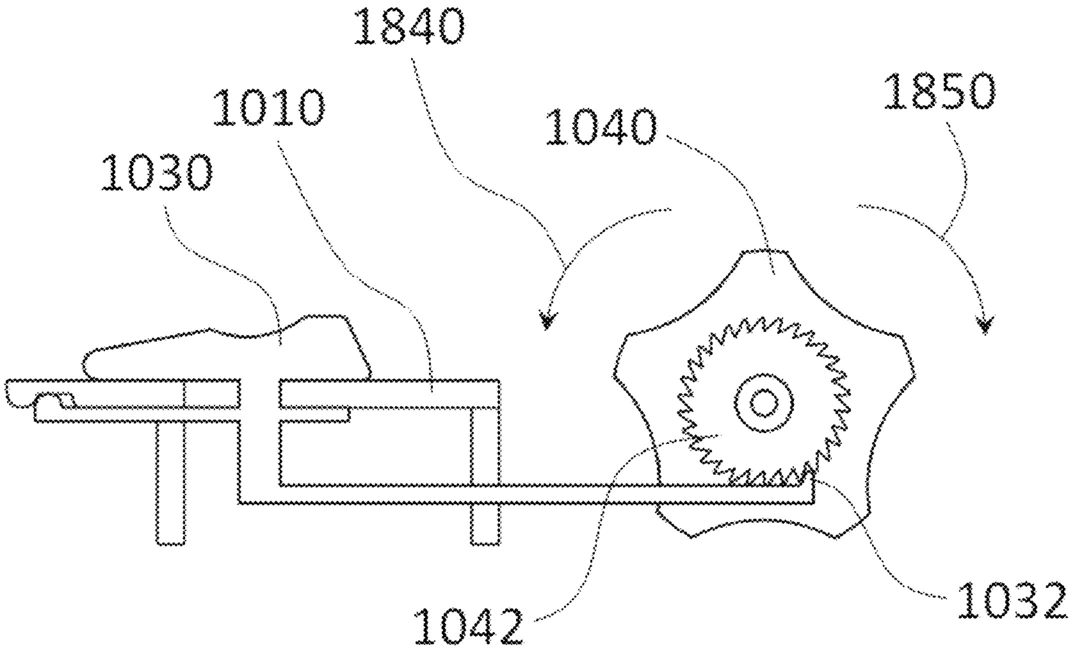
FIG. 10D is a schematic diagram showing a wire controller and a second securing portion of the spine stabilization system in accordance with an embodiment of the present invention.

Please refer to FIGS. 10A, 10B and 10D, wherein FIG. 10D is a schematic diagram showing a wire controller and a second securing portion of the spine stabilization system in accordance with an embodiment of the present invention. As the embodiment in FIG. 10D shows, the wire controller 1040 comprises a first securing portion 1042. The auxiliary fixation device comprises a second securing portion 1030, which is disposed on the main body portion 1010 and can move relative to the main body portion. Specifically, when the second securing portion 1030 is in a first state, the second securing portion 1030 is in contact with the first securing portion 1042, thereby preventing the wire controller 1040 from moving relative to the main body portion 1010 in a first direction 1840 and/or a second direction 1850, which is opposite to the first direction 1840. When the second securing portion 1030 is in a second state, the second securing portion 1030 and the first securing portion 1042 are apart from each other; at this time, the wire controller 1040 can move relative to the main body portion 1010 in the first direction 1840 or in the second direction 1850 opposite to the first direction 1840 according to the needs.

Preferably, the first securing portion 1042 is a gear portion disposed on the wire controller 1040. The second securing portion 1030 comprises a protruding block 1032. Specifically, when the second securing portion 1030 is in the first state, the protruding block 1032 of the second securing portion 1030 is pressed against the first securing portion 1042, so that the wire controller 1040 is unable to move relative to the main body portion 1010 in the first direction 1840 and/or the second direction 1850 opposite to the first direction 1840. Preferably, the second securing portion 1030 can be partially disposed outside the main body portion 1010, so that the user can easily set the second securing portion 1030 to the first state or the second state. It should be understood that the structures and arrangements of the aforementioned stop portion, first stop portion and second stop portion can be similar to those of the second securing portion 1030, but are not limited thereto.

Figure 11:
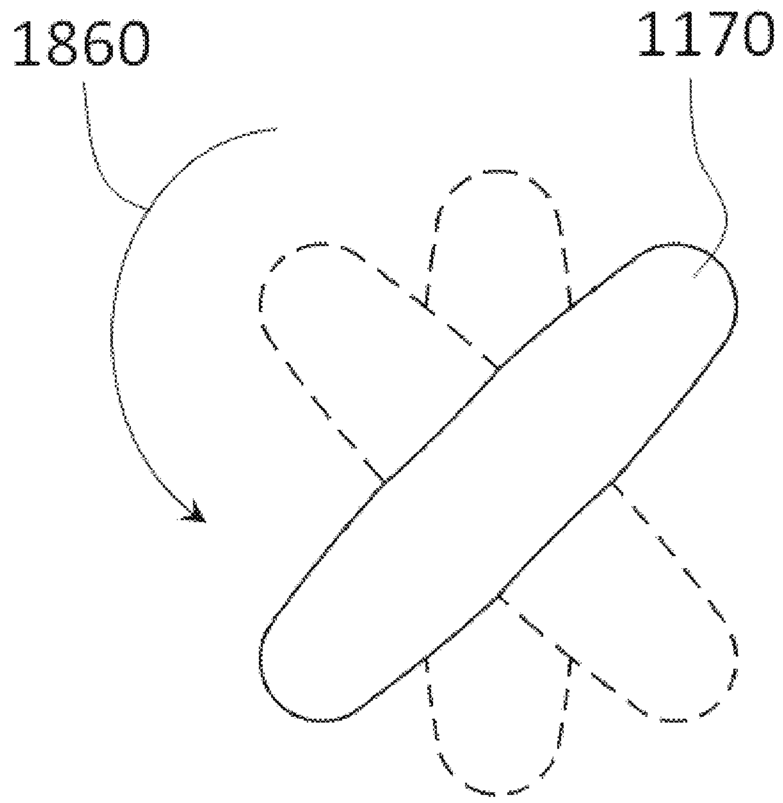
FIG. 11 is a schematic diagram showing a fixation member of the spine stabilization system in accordance with an embodiment of the present invention.

Please refer to FIG. 11, which is a schematic diagram showing a fixation member of the spine stabilization system in accordance with an embodiment of the present invention. As the embodiment in FIG. 11 shows, after a fixation member 1170 punctures and penetrates a target spinal ligament, the orientation of the fixation member 1170 may be adjusted to fixate it to the target spinal ligament. For example, the fixation member 1170 may be rotated in a direction 1860 to fixate it to the target spinal ligament.

The spine stabilization system of the present invention is disclosed in conjunction with the description and accompanying drawings above. However, it should be understood that the embodiments of the present invention are for illustrative purposes only and may be modified without departing from the scope and spirit of the present invention, and that such modifications should be within the scope of the claims of the present invention. Therefore, the embodiments described herein should not be construed as limiting the scope of the invention, and the actual scope and spirit of the present invention are disclosed in the claims hereinafter.

What is claimed is:

1. A spine stabilization system, comprising:

a wire having a first wire end and a second wire end;

a first fixation member connected to the first wire end;

a wire controller, the second wire end being connected to the wire controller, and a portion of the wire being movably disposed on the wire controller;

a first auxiliary fixation device comprising a needle portion and a first receiving portion, and a second auxiliary fixation device comprising a second receiving portion;

wherein when the spine stabilization system is in a first state of use, the wire together with the wire controller are detachably connected to the first auxiliary fixation device;

wherein when the spine stabilization system is in the first state of use, the wire is partially received in the needle portion, and the wire controller is connected to the first receiving portion of the first auxiliary fixation device;

wherein when the spine stabilization system is in a second state of use, the first fixation member is fixated to a target spinal ligament, and the wire together with the wire controller are detachably connected to the second auxiliary fixation device;

wherein when the spine stabilization system is in the second state of use, the wire controller is connected to the second receiving portion of the second auxiliary fixation device.

2. The spine stabilization system of claim 1, wherein the wire is elastic.

3. The spine stabilization system of claim 1, wherein the needle portion is provided with a slot extending thereon, and the wire extends from the slot to the outside of the needle portion and is connected to the wire controller.

4. The spine stabilization system of claim 1, wherein the wire controller comprises a gear portion contacting the first receiving portion, and the wire controller is prevented from moving relative to the first receiving portion in a particular direction by means of the gear portion.

5. The spine stabilization system of claim 1, wherein the wire controller comprises a rod portion and the first receiving portion of the first auxiliary fixation device comprises a first open slot; and wherein when the spine stabilization system is in the first state of use, the wire controller is detachably connected to the first open slot of the first auxiliary fixation device by means of the rod portion.

6. The spine stabilization system of claim 1, wherein the first auxiliary fixation device comprises a pushing mechanism, and the first auxiliary fixation device pushes the first fixation member outward from within the needle portion by means of the pushing mechanism, so that the first fixation member is fixated to a target spinal ligament.

7. The spine stabilization system of claim 6, wherein the pushing mechanism is that the first auxiliary fixation device consists of a push rod and a push rod passage, and the push rod passage communicates with the needle portion; and wherein the push rod enters the needle portion through the push rod passage and pushes the first fixation member outward from within the needle portion.

8. The spine stabilization system of claim 1, further comprising:

a plurality of second fixation members, each second fixation member being connected to the wire individually, wherein when the spine stabilization system is in the first state of use, at least one among the first fixation member and the plurality of second fixation members is received in the needle portion.

9. The spine stabilization system of claim 8, wherein the first fixation member comprises a first puncture portion and a first connection portion, and the first fixation member is connected to the wire through the first connection portion; and wherein each of the plurality of second fixation members comprises a second puncture portion and a second connection portion, and each second fixation member is connected to the wire through a corresponding second connection portion.

10. The spine stabilization system of claim 8, wherein the first auxiliary fixation device comprises a pushing mechanism, and the first auxiliary fixation device pushes one among the first fixation member and the plurality of second fixation members outward from within the needle portion by means of the pushing mechanism, so that the first fixation member and/or the second fixation member is fixated to a target spinal ligament.

11. The spine stabilization system of claim 1, wherein the second auxiliary fixation device comprises a wire securing member and a securing mechanism, and the second auxiliary fixation device secures the wire between the wire securing member and a target connecting rod by means of the securing mechanism.

12. The spine stabilization system of claim 1, wherein the wire controller comprises a rod portion and the second auxiliary fixation device comprises a second open slot; and wherein when the spine stabilization system is in the second state of use, the wire controller is detachably connected to the second open slot of the second auxiliary fixation device by means of the rod portion.

13. A spine stabilization system, comprising:

a wire;

a first fixation member connected to the wire; and an auxiliary fixation device, comprising:

a main body portion;

a needle portion connected to the main body portion, wherein a portion of the wire is disposed within the needle portion, and the wire and the first fixation member are able to move relative to the needle portion;

a push rod portion partially arranged in the needle portion and is able to move relative to the needle portion;

a control portion connected to the push rod portion; and a wire controller connected to the main body portion, the wire controller being able to move relative to the main body portion;

wherein the control portion causes the push rod portion to move relative to the needle portion, so that the wire and the first fixation member move relative to the needle portion by means of the push rod portion;

wherein the first fixation member is connected to a first wire end of the wire;

wherein a second wire end of the wire is connected to the wire controller, and a portion of the wire is movably disposed on the wire controller;

wherein the wire controller comprises a first securing portion, and the auxiliary fixation device comprises a second securing portion provided on the main body portion, the second securing portion being able to move relative to the main body portion;

wherein when the second securing portion is in a first state, the second securing portion contacts the first securing portion, so that the wire controller is unable to move relative to the main body portion in a first direction;

wherein when the second securing portion is in a second state, the second securing portion and the first securing portion are apart from each other, so that the wire controller can move relative to the main body portion in the first direction or in a second direction opposite to the first direction.

14. The spine stabilization system of claim 13, wherein the control portion has a first thread, the push rod portion has a second thread, and the control portion is threadedly connected to the second thread of the push rod portion through the first thread; and wherein threaded engagement and relative movement between the control portion and the push rod portion causes the push rod portion to move relative to the needle portion.

15. The spine stabilization system of claim 13, wherein the control portion is connected to the main body portion and is able to move relative to the main body portion.

16. The spine stabilization system of claim 13, wherein the main body portion comprises a groove portion having a groove extension direction;

wherein the push rod portion comprises a groove connection portion partially disposed in the groove portion; and wherein the push rod portion moves relative to the main body portion along the groove extension direction by means of the groove connection portion.

17. The spine stabilization system of claim 13, wherein the needle portion is provided with a slot extending thereon, and the wire extends from the slot to the outside of the needle portion and is connected to the wire controller.

18. The spine stabilization system of claim 13, wherein the first securing portion is a gear portion provided on the wire controller.

19. The spine stabilization system of claim 13, wherein the wire is elastic.

20. The spine stabilization system of claim 13, further comprising:

a plurality of second fixation members, each second fixation member being connected to the wire individually, wherein at least one among the first fixation member and the plurality of second fixation members is received in the needle portion.

21. The spine stabilization system of claim 13, wherein the first fixation member comprises a puncture portion and a connection portion, and the first fixation member is connected to the wire through the connection portion.

* * * * *